(12) United States Patent
Ho (10) Patent No.: US 9,382,530 B2
(45) Date of Patent: Jul. 5, 2016

(54) METHOD AND DEVICE FOR ENHANCING A DIRECTIONAL MIGRATION OF STEM CELLS

(71) Applicant: TAIPEI MEDICAL UNIVERSITY, Taipei (TW)

(72) Inventor: Jennifer Hui-Chun Ho, Taipei (TW)

(73) Assignee: TAIPEI MEDICAL UNIVERSITY, Taipei (TW)

( * ) Notice: Subject to any disclaimer, the term of this patent is extended or adjusted under 35 U.S.C. 154(b) by 0 days.

(21) Appl. No.: 14/068,969

(22) Filed: Oct. 31, 2013

(65) Prior Publication Data

US 2014/0377831 A1 Dec. 25, 2014

(30) Foreign Application Priority Data

Jun. 19, 2013 (TW) .............................. 102121851 A (51) Int. Cl.
| | |
|---|---|
| C12N 13/00 | (2006.01) |
| C12M 1/00 | (2006.01) |
| C12M 1/42 | (2006.01) |
| C12M 1/34 | (2006.01) |
| C12N 5/0775 | (2010.01) |

(52) U.S. Cl.
CPC ............... *C12N 13/00* (2013.01); *C12M 31/00* (2013.01); *C12M 35/00* (2013.01); *C12M 41/46* (2013.01); *C12N 5/0667* (2013.01); *C12N 2510/00* (2013.01); *C12N 2529/10* (2013.01)

(58) Field of Classification Search
None
See application file for complete search history.

(56) References Cited

U.S. PATENT DOCUMENTS

| | | | |
|---|---|---|---|
| 7,365,172 B2 | 4/2008 | Twardzik et al. | |
| 8,273,756 B2 | 9/2012 | Sugaya et al. | |
| 2012/0288480 A1 | 11/2012 | Ho | |

OTHER PUBLICATIONS

Xiaobo Liang et al., Delayed Cutaneous Wound Healing and Aberrant Expression of Hair Follicle Stem Cell Markers in Mice Selectively Lacking Ctip2 in Epidermis, PLoS One., Feb. 2012, vol. 7., Issue 2, e29999.
Yaojiong Wu, MD, PhD et al., Bone marrow-derived stem cells in wound healing: a review, Wound Rep Reg, 2007, vol. 15, pp. S18-S26.
Xiaobing Fu, MD et al., Migration of bone marrow-derived mesenchymal stem cells induced by tumor necrosis factor-a and its possible role in wound healing, Wound Rep Reg, 2009, vol. 17, pp. 185-191.
Cai Huang et al., MAP kinases and cell migration, Journal of Cell Science, 2004, vol. 117, 4619-4628.

Chung Neon Ryu et al., Migration of human umbilical cord blood mesenchymal stem cells mediated by stromal cell-derived factor-1/CXCR4 axis via Akt, ERK, and p38 signal transduction pathways, Biochemical and Biophysical Research Communications 398 (2010) 105-110.
Wei Liu et al., Rho GTPases in Hematopoietic Stem/Progenitor Cell Migration, Methods in Molecular Biology, vol. 750, pp. 307-319.
Elke M. Vinck, P.T. et al.,Green Light Emitting Diode Irradiation Enhances Fibroblast Growth Impaired by High Glucose Level, Photomedicine and Laser Surgery, vol. 23, No. 2, 2005, pp. 167-171.
Tomohiro Fushimi, MD et al., Green light emitting diodes accelerate wound healing: Characterization of the effect and its molecular basis in vitro and in vivo, Wound Rep Reg, 2012, vol. 20, pp. 226-235.
Hongran Choi et al., Inflammatory cytokines are suppressed by light-emitting diode irradiation of P. gingivalis LPS-treated human gingival fibroblasts, Lasers Med Science, 2012, vol. 27, pp. 459-467.
Hyung Keun Kim et al., Red light of 647 nm enhances osteogenic differentiation in mesenchymal stem cells, Lasers Med Science, 2009, vol. 24, pp. 214-222.
Wen-Tung Li, Ph.D. et al., Red-Light Light-Emitting Diode Irradiation Increases the Proliferation and Osteogenic Differentiation of Rat Bone Marrow Mesenchymal Stem Cells, Photomedicine and Laser Surgery, vol. 28, Supplement 1, 2010, pp. s157-s165.
Fei Peng et al., The effect of noncoherent red light irradiation on proliferation and osteogenic differentiation of bone marrow mesenchymal stem cells, Lasers Med Science, 2012, vol. 27, pp. 645-653.
Jason P. Weick et al., Functional control of transplantable human ESC-derived neurons via optogenetic targeting, Stem Cells, Nov. 2010, vol. 28(11), pp. 1-16.
Albrecht Stroh et al., Tracking Stem Cell Differentiation in the Setting of Automated Optogenetic Stimulation, Stem Cells, 2011, vol. 29, pp. 78-88.
Wei-Kee Ong et al., The activation of directional stem cell motility by green light-emitting diode irradiation, Biomaterials, vol. 34, 2013, pp. 1911-1920.
Office Action from Taiwan Intellectual Property Office dated Oct. 27, 2014 for corresponding Taiwan Patent Application No. 102121851.
English translation of the Office Action from Taiwan Intellectual Property Office dated Oct. 27, 2014 for corresponding Taiwan Patent Application No. 102121851.
Fushimi T. et al., Green light emitting diodes accelerate wound healing: characterization of the effect and its molecular basis in vitro and in vivo., Wound Repair Regen. Mar.-Apr. 2012;20(2):226-35.

(Continued)

*Primary Examiner* — Renee Claytor
*Assistant Examiner* — David Berke-Schlessel
(74) *Attorney, Agent, or Firm* — WPAT, P.C., Intellectual Property Attorneys; Anthony King (57) ABSTRACT

The invention provides a method of enhancing a directional migration of stem cells, comprising providing one or more stem cell(s) and irradiating the stem cells with an effective energy of green light thereby enhancing stem cell directionally migrating, wherein the orientation of migration of stem cells is opposite to the green light source. Also provided is a stem cell treated by the method of the invention and a device for enhancing a directional migration of stem cells.

10 Claims, 11 Drawing Sheets

(56) References Cited

OTHER PUBLICATIONS

Anton, K. et al., Macrophage-associated mesenchymal stem cells assume an activated, migratory pro-inflammatory phenotype with increased IL-6 and CXCL10 secretion, PLOS One. 2012;7(4):e35036.

Ryu, Chung Heon et al. Migration of human umbilical cord blood mesenchymal stem cells mediated by stromal cell-derived factor-1/CXCR4 axis via Akt, ERK and P38 signal transduction pathways, Biochem Biophys Res Commun. Jul. 16, 2010:398(1): 105-10.

Liu, W. et al., Rho GTPases in hematopoietic stem/progenitor cell migration, Methods Mol Biol. 2011;750:307-19.

Terakita, A., The opsins, Genome Biol. 2005; 6(3): 213. Epub Mar. 1, 2005.

US20120288480 is the counterpart US application for Taiwan publication 201235471.

METHOD AND DEVICE FOR ENHANCING A DIRECTIONAL MIGRATION OF STEM CELLS

FIELD OF THE INVENTION

The invention pertains to a method and related device for enhancing a directional migration of stem cells. Particularly, the invention provides a method and related device of using green light irradiation to enhance a directional migration of stem cells.

BACKGROUND OF THE INVENTION

Stem cells are generally classified according to their origin, essentially adult, embryonic or neonatal origin. Since stem cells are capable of differentiating into a broad variety of cell types, they play an important role in the healing and regenerative processes of various tissues and organs. Enhanced efficacy of stem cell engraftment could improve the outcome of clinical transplantations as well as gene therapy protocols, and might be achieved by modulating the ability of stem cells to home to and repopulate the recipient target. Homing of stem cells and the subsequent inhibition of inflammation are critical for acute wound repair (Liang X et al., *PLoS One.* 2012; 7:e29999; Wu Y et al., *Wound Repair Regen.* 2007; 15 Suppl 1:S18-26; and Fu X et al., *Wound Repair Regen.* 2009; 17:185-91), and directional stem cell migration leads to an effective and specific tissue repair (Huang C et al., *J Cell Sci.* 2004; 117:4619-28). U.S. Pat. No. 7,365,172 provides a peptide derived from a loop or "lollipop" region of transforming growth factor alpha and is biologically active for causing stem cells to proliferate and migrate. U.S. Pat. No. 8,273,756 provides cells and methods for stimulating proliferation and migration of endogenous and exogenous mammalian stem cells in vivo and in vitro. Ras homolog gene family, member A (RhoA) is essential for cell migration to regulate actin cytoskeleton reorganization and activation of extracellular regulated kinase (ERK), p38 in stem cells has been reported to crucial for their directional migration induced by pro-inflammatory cytokines, chemokines or stromal cell-derived factor-1 (Fu X et al., *Wound Repair Regen.* 2009; 17:185-91; Ryu C H et al., *Biochem Biophys Res Commun.* 2010; 398: 105-10; Liu W et al., *Methods Mol Biol.,* 2011; 750:307-19), all of which lead to a high specificity and therapeutic efficiency of stem cells in wound repair.

Light provides both illumination and thermal energy. Light exposure is physiologically responsible for human homeostasis such as vitamin D synthesis, sleep-wake cycle, and vision. In addition, phototherapy is a standard treatment for skin disorders, neovascular retinopathy, or musculoskeletal disorder, with the uses of appropriate wavelength, intensity and duration of light exposure. It is known in the art that green light emitting diode (LED) irradiation enhances fibroblast growth impaired by high glucose level (Elke M. Vinck et al., *Photomedicine and Laser Surgery,* Volume 23, Number 2, 2005, pp. 167-171) and promotes the wound healing by inducing HaCat keratinocytes migratory and proliferative mediators (Tomohiro Fushimi et al., *Wound Repair and Regeneration,* 2012, 20: 226-235). However, HongRan Choi et al., indicate that red LED irradiation can inhibit activation of pro-inflammatory cytokines, mediate the MAPK signaling pathway, and may be clinically useful as an anti-inflammatory tool (HongRan Choi et al., *Lasers Med. Sci.* (2012), 27:459-467). Recently, red/NIR LED irradiation has been found to promote MSCs growth and enhance their osteogenic differentiation ability (Kim H K et al., *Lasers Med. Sci.* 2009; 24:214-22; Li W T et al., *Photomed Laser Surg.* 2010; 28 Suppl 1:S157-65; and Peng F et al., *Lasers Med. Sci.* 2012; 27:645-53). It has been demonstrated that over-expression of channelrhodopsin-2 (ChR2) in embryonic stem cells successfully differentiates into functional excitatory neuron under blue LED irradiation (Weick J P et al, *Stem cells.* 2010; 28:2008-16 and Stroh A et al., *Stem cells.* 2011; 29:78-88). However, the mechanism(s) of red/NIR or blue LED irradiation regulating stem cell behavior remains elucidative.

There thus exists a need to explore the effect of light in the enhancement of stem cell migration ability which will be valuable for tissue regeneration or transplantation.

SUMMARY OF THE INVENTION

The invention provides a method of enhancing a directional migration of stem cells, comprising providing one or more stem cell(s) and irradiating the stem cells with an effective energy of green light thereby enhancing stem cell directionally migrating, wherein the orientation of migration of stem cells is opposite to the green light source. Preferably, the irradiation of green light is provided at an energy level of about 0.5 J/cm$^2$ to about 30 J/cm$^2$. Preferably, the green light source is provided by green light emitting diode (LED), green fluorescence or laser. Preferably, the stem cells are embryonic stem cells or adult stem cells.

The invention also provides a stem cell treated by the method of the invention. The stem cells treated by the method of the invention have higher ATP contents than the stem cell untreated by the method of the invention. The p38, ERK 1/2, c-Jun N-terminal kinase (JNK), MAP kinase kinase (MEK) 1/2, Akt, cAMP response element-binding (CREB), Yes and c-Jun the resulting stem cells are activated. The Lyn, signal transducer and activator of transcription (STAT) 5 alpha, and p70S6 kinase of the resulting stem cells are inhibited. The expression of RRH, OPN1SW and OPN3 of the resulting stem cells are induced by green light.

The invention further provides a device for enhancing a directional migration of stem cells, comprising one or multiple layers of container for holding stem cells and one or multiple layers of one of more green light sources providing an energy level at from about 0.5 J/cm$^2$ to about 30 J/cm$^2$ at the cell surfaces when irradiation, wherein in each layer the green light source is disposed opposite to the stem cells. When plural containers are used, the containers are layer-by-layer arranged and each container is disposed from a green light source and located at opposite position to the green light.

DETAILED DESCRIPTION OF THE INVENTION

A feature which makes stem cells promising candidates for cell therapy is their ability to migrate effectively into damaged or diseased tissues. The invention surprisingly found that green light irradiation can enhance directional migration of stem cells. Accordingly, the invention develops a non-invasive, light-driving method to enhance stem cell migration ability which will be valuable for tissue regeneration and transplantation.

As used herein, "stem cells" are cells that possess self-renewal ability and multiple differentiation ability when exposed to specific environmental conditions. Self-renewal means that during cell division, at least one of the two daughter cells will be a stem cell.

As used herein, "isolated," used in reference to a single cell or cell population, means that the cell or cell population is substantially free of other cell types or cellular material with which it naturally occurs in the orbital fat.

As used herein, "effective amount of energy" of green light used in reference to an amount of energy provided by green light, which is capable of enhancing directional migration, directional mobilization and/or homing of stem cells, that can be determined by various methods used in the biological sciences. The terms "directional migration" and "directional mobilization" can be used interchanged herein, which denotes directional orientation of migrating of stem cells. Directional migration requires the coordination of cytoskeletal changes essential for cell polarization and adhesion turnover. In one embodiment, an "effective amount of energy" is an energy level effective for enhancing mobilization of stem cells that replenish, repair, or rejuvenate tissue. In another embodiment, an "effective amount of energy" is an energy level effective for enhancing directional migration of stem cells. In still another embodiment, an "effective amount of energy" is an energy level effective for enhancing homing of stem cells from the circulatory system to various tissues or organs.

In one aspect, the invention provides a method of enhancing a directional migration of stem cells, comprising providing one or more stem cell(s) and irradiating the stem cells with an effective energy of green light thereby enhancing stem cell directionally migrating, wherein the orientation of migration of stem cells is opposite to the green light source. Preferably, the irradiation of green light is provided at an energy level of about 0.5 $J/cm^2$ to about 30 $J/cm^2$. More preferably, the energy level is 0.5 $J/cm^2$ to about 25 $J/cm^2$, 0.5 $J/cm^2$ to about 20 $J/cm^2$, 0.5 $J/cm^2$ to about 15 $J/cm^2$, about 1 $J/cm^2$ to about 30 $J/cm^2$, 1 $J/cm^2$ to about 25 $J/cm^2$, about 1 $J/cm^2$ to about 20 $J/cm^2$, about 1 $J/cm^2$ to about 15 $J/cm^2$, about 1 $J/cm^2$ to about 12 $J/cm^2$, about 1.5 $J/cm^2$ to about 30 $J/cm^2$, about 1.5 $J/cm^2$ to about 25 $J/cm^2$, about 1.5 $J/cm^2$ to about 20 $J/cm^2$, about 1.5 $J/cm^2$ to about 15 $J/cm^2$, about 1.95 $J/cm^2$ to about 30 $J/cm^2$, about 1.95 $J/cm^2$ to about 25 $J/cm^2$, about 1.95 $J/cm^2$ to about 20 $J/cm^2$, about 1.95 $J/cm^2$ to about 15 $J/cm^2$, about 1.95 $J/cm^2$ to about 12 $J/cm^2$. More preferably, the energy level is about 1.95 $J/cm^2$ to about 11.4 $J/cm^2$.

The energy level is calculated according to the formula: Energy (J/cm)=intensity on cell surface ($W/cm^2$)×irradiation time (s); wherein "J" refers to Joule, "s" refers to second and "W" refers to Watt. Preferably, the intensity ranges from about 5 $\mu W/cm^2$ to about 80 $\mu W/cm^2$; more preferably, 5 $\mu W/cm^2$ to about 70 $\mu W/cm^2$, 5 $\mu W/cm^2$ to about 75 $\mu W/cm^2$, 5 $\mu W/cm^2$ to about 70 $\mu W/cm^2$, 5 $\mu W/cm^2$ to about 66 $\mu W/cm^2$, 10 $\mu W/cm^2$ to about 80 $\mu W/cm^2$, 10 $\mu W/cm^2$ to about 75 $\mu W/cm^2$, 10 $\mu W/cm^2$ to about 70 $\mu W/cm^2$ or 10 $\mu W/cm^2$ to about 66 $\mu W/cm^2$. Preferably, the irradiation time ranges from about 1 second to about 72 hours; more preferably, about 30 seconds to about 72 hours, about 60 seconds to about 72 hours, about 5 minutes to about 72 hours, about 10 minutes to about 72 hours, about 20 minutes to about 72 hours, about 30 minutes to about 72 hours, about 40 minutes to about 72 hours, about 50 minutes to about 72 hours, about 1 hour to about 72 hours, about any of about 2 hours to about 72 hours, 1 second to about 48 hours; more preferably, about 30 seconds to about 48 hours, about 60 seconds to about 48 hours, about 5 minutes to about 48 hours, about 10 minutes to about 48 hours, about 20 minutes to about 48 hours, about 30 minutes to about 48 hours, about 40 minutes to about 48 hours, about 50 minutes to about 48 hours, about 1 hour to about 48 hours, or about any of about 2 hours to about 48 hours.

According to the invention, any light source illuminating green light can be used in the invention. The wavelength of green light is at about 520 nm to 550 nm. Preferably, the green light source is provided by green light emitting diode (LED), green fluorescence or laser. The examples of green LED include but not limited to RGB LED, phosphor-based white LED, organic LED or quantum dot Led. The examples of laser include but not limited to green laser, diode pumped solid state (DPSS) laser, gas laser or gas dye laser. The examples of the gas laser include but not limited to the helium-neon laser (543 nm), the argon-ion laser (514 nm) and the krypton-ion laser (521 nm and 531 nm). The examples of green fluorescence include but not limited to fluorescein, oregon green, BODIPY-FL or rhodamine green.

Non-limiting examples of stem cells, which can be used according to this aspect of the present invention, are embryonic stem cells and adult stem cells. The adult stem cells include but not limited to hematopoietic stem cells (HSCs), mesenchymal stem cells (MSCs) adipose-derived stem cell, endothelial stem cell and dental pulp stem cells. Preferably, the stem cells are orbital fat stem cells (OFSCs).

It will be appreciated that commercially available stem cells can be also be used according to this aspect of the present invention. Human ES cells can be purchased from the NIH human embryonic stem cells registry (<http://escr.nih.gov>). Non-limiting examples of commercially available embryonic stem cell lines are BG01, BG02, BG03, BG04, CY12, CY30, CY92, CY10, TE03, and TE32.

In another aspect, the invention provides a stem cell treated by the method of the invention. The stem cells treated by the method of the invention have higher ATP contents than the stem cell untreated by the method of the invention. Moreover, p38, ERK 1/2, c-Jun N-terminal kinase (INK), MAP kinase kinase (MEK) 1/2, Akt, cAMP response element-binding (CREB), Yes and c-Jun the stem cells treated by the method of the invention are activated. In addition, Lyn, signal transducer and activator of transcription (STAT) 5 alpha, and p70S6 kinase of the stem cells treated by the method of the invention are inhibited. The expression of RRH, OPN1SW and OPN3 of the stem cells treated by the method of the invention are induced by green light.

In a further aspect, the invention provides a device for enhancing a directional migration of stem cells, comprising one or multiple layers of container for holding stem cells and one or multiple layers of one of more green light sources providing an energy level at from about 0.5 J/cm$^2$ to about 30 J/cm$^2$ at the cell surfaces when irradiation, wherein in each layer the green light source is disposed opposite to the stem cells. The energy level provided by the green light is described above. The distance between the green light and the stem cells and the light intensity provided by the green light are various in combination as long as the green light provides an energy level at from about 0.5 J/cm$^2$ to about 30 J/cm$^2$ at the cell surfaces when irradiation. In addition, the device of the invention can further comprises a electric power connecting with a layer of green light source.

According to the invention, any transparent container can be used in the invention. Preferably, the container is a flask, a resin plate, a glass plate, a cell culture chamber or microwell plate. Preferably, the container is a flask or a glass plate. When multiple layers of containers are used, the containers are layer-by-layer arranged and each container is disposed with a green light source or green light source array and the container located at opposite position to the green light.

The device of the invention can includes one or multiple layers of green light source. In one embodiment, the green light source is disposed in a holder for fixing the green light source and the holder is composed by a light proof material. The green light source used in the invention is described above. In one embodiment, the green light source is provided with a single green fluorescence device or LED device. In another embodiment, when plural green light sources are used, they can be arranged in an array form.

Figure 8:
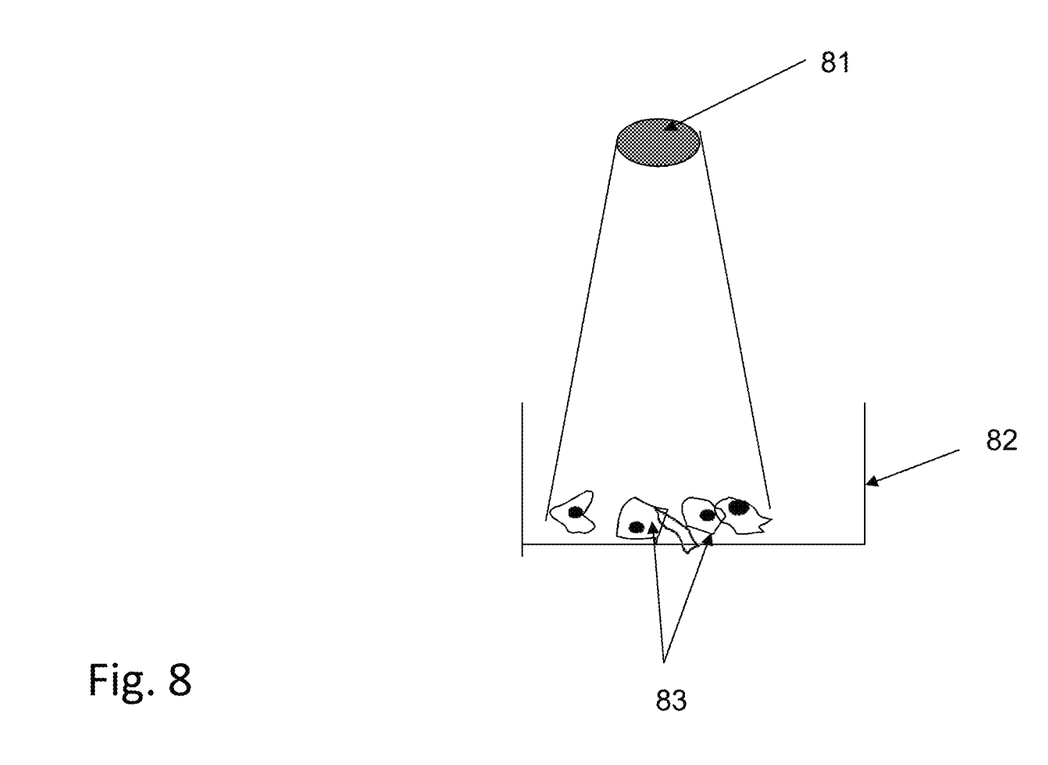
FIG. 8 is an illustrative view of a general device of the invention.

FIG. 8 is an illustrative figure of a general device of the invention. Referring to FIG. 8, stem cells 83 are cultured in a container 82 and the green fluorescence or green LED 81 irradiates green light to the stem cells 83.

Figure 9:
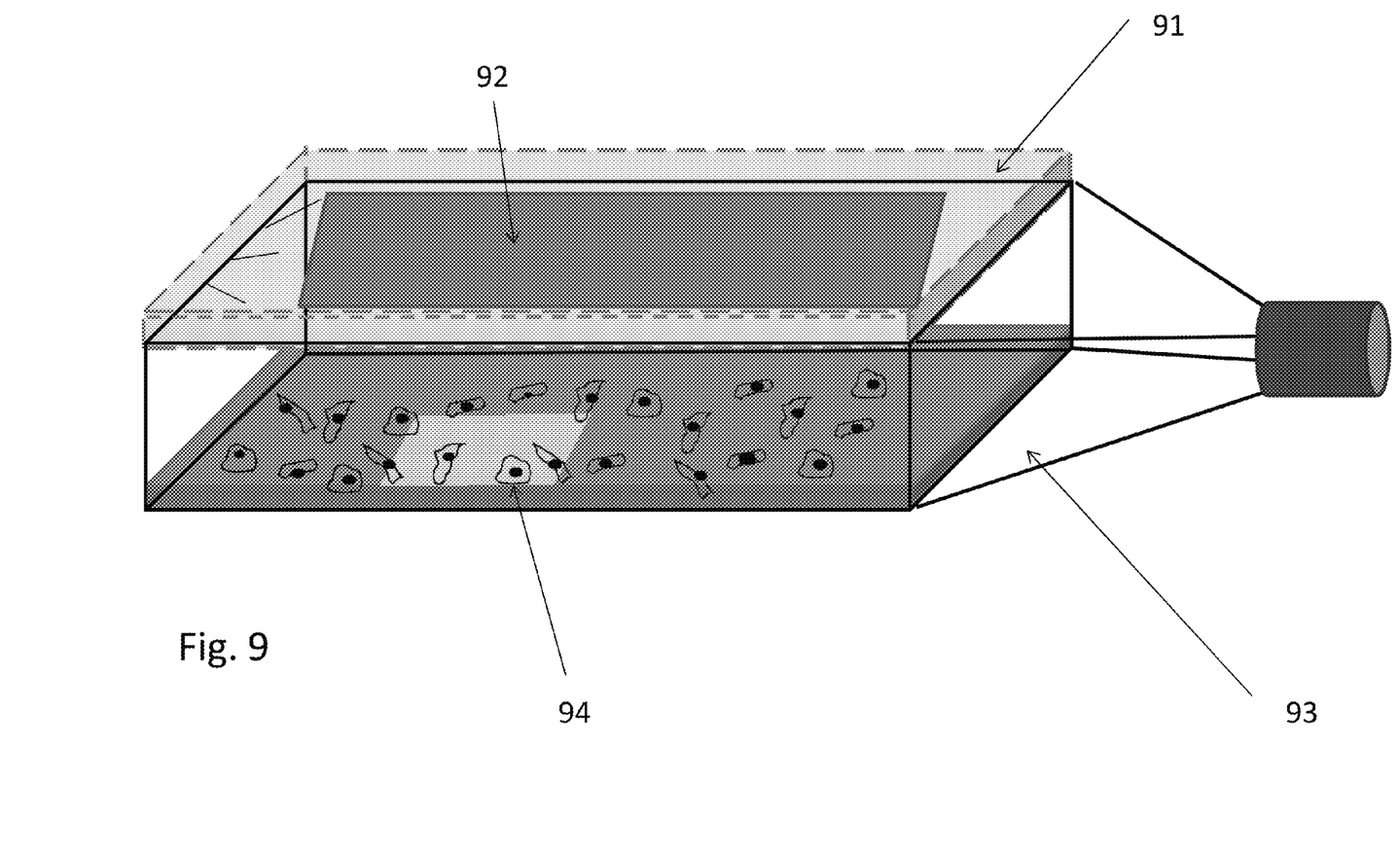
FIG. 9 is an illustrative view of one embodiment of the device of the invention (a single light source).
Figure 10:
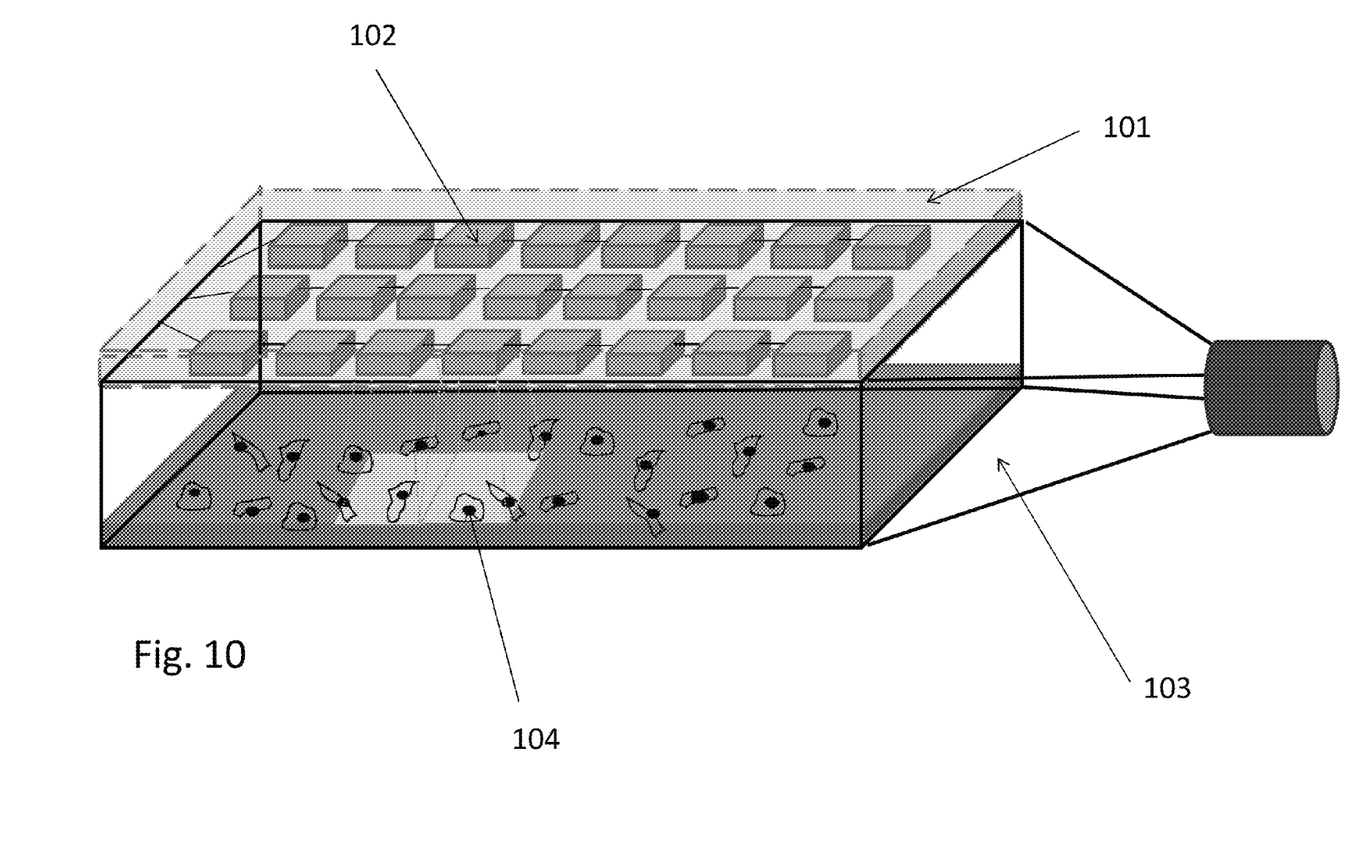
FIG. 10 is an illustrative view of another embodiment of the device of the invention (multiple light sources in array form).
Figure 11:
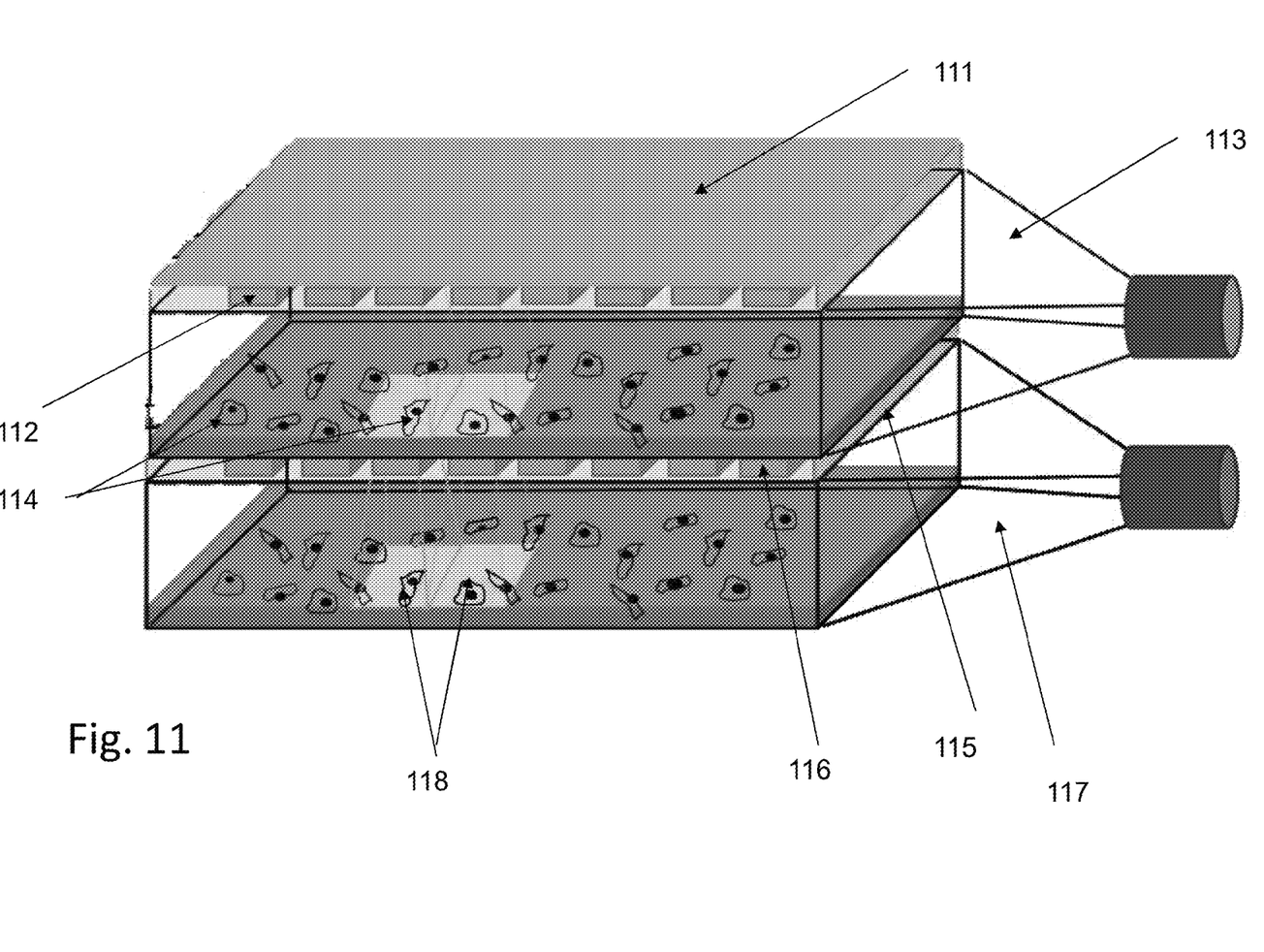
FIG. 11 is an illustrative view of a further embodiment of the device of the invention (multiple layers of multiple light sources in array form in combination with multiple containers).

FIGS. 9 to 11 are illustrative views of the preferred embodiments of the device of the invention. Referring to FIG. 9 showing a single light source, a holder 91 is provided to fix a piece of green fluorescence or green LED 92. The stem cells 94 are cultured in a flask container 93 and the green fluorescence or green LED 92 irradiates green light to the stem cells 94. Referring to FIG. 10 showing light source in array form, a holder 101 is provided to fix an array of green LEDs 102. The stem cells 104 are cultured in a flask container 103 and the LEDs 102 irradiate green light to the stem cells 104.

Referring to FIG. 11 showing two layers of light sources in combination with containers, in the upper layer, a holder 111 is provided to fix an array of green LEDs 112. The stem cells 114 are cultured in a flask container 113 and the LEDs 112 irradiate green light to the stem cells 114; in the bottom layer, a holder 115 is provided to fix an array of green LEDs 116. The stem cells 118 are cultured in a flask container 117 and the LEDs 116 irradiate green light to the stem cells 118. In one embodiment of the invention, the green light source can be a single green light source. When multiple layers of green light sources are used, each layer has an electric power.

In each of the above embodiments, the device can further comprises one or more electric power.

The invention explores the effect as well as mechanism of green light irradiation on directional migration of stem cells. Through the comparison of migrated cells with non-migrated cells under green, red light exposure or heat, the mechanism controlling green light irradiation-induced cell migration and the role of adenosine triphosphate (ATP) in stem cell migration are elucidated. The photosensitizers responsible for green light irradiation-induced motility in OFSCs were also delineated in this invention.

EXAMPLE

Methods and Materials

Cells Isolation and Culture

OFSCs were isolated from human orbital fat tissues with informed consent. Approval from the Institutional Review Board of Wan Fang Hospital, Taipei Medical University was obtained prior to the commencement of the experiments. The procedures of isolating OFSCs were described in Ho J H et al, *Tissue Eng Part A*. 2011; 17:255-66. Briefly, adipose tissues were fragmented, digested, and filtered. After centrifugation, the cells from the resulting pellet were plated in non-coated tissue culture flasks (BD Biosciences, San Jose, Calif., USA) with MesenPro medium (Invitrogen, Carlsbad, Calif., USA). Cells with colony formation ability, MSC surface phenotype profile, and tri-linage differentiation capacity were defined as OFSCs. The OFSCs were maintained in MesenPro medium (Invitrogen) under non-contact culture as described in Ho J H et al., CellTransplant. 2011; 20:1209-20. Briefly, cells from one flask were detached when their density reached 60-70% of confluence, and were re-seeded into three new flasks. Eighth to tenth passage of OFSCs were used for the experiments.

SV-40 immortalized human corneal epithelial (HCE-T) cells (Araki-Sasaki K et al., *Invest Ophthalmol Vis Sci*. 1995; 36:614-21) were kindly given by Dr. Araki-Sasaki. The cells were cultured in DMEM/HamF12 (1:1) medium supplemented with 5% fetal bovine serum (HyClone, Logan, Utah, USA), 5 μg/ml insulin, 0.1 μg/ml cholera toxin (Sigma-Aldrich, St. Louis, Mo., USA), 10 ng/ml recombinant human epidermal growth factor (hEGF) (BD Biosciences), and 0.5% DMSO, as previous described in Ho J H et al., *Invest Ophthalmol Vis Sci*. 2007; 48:27-33.

LED Photosystem

Figure 1:
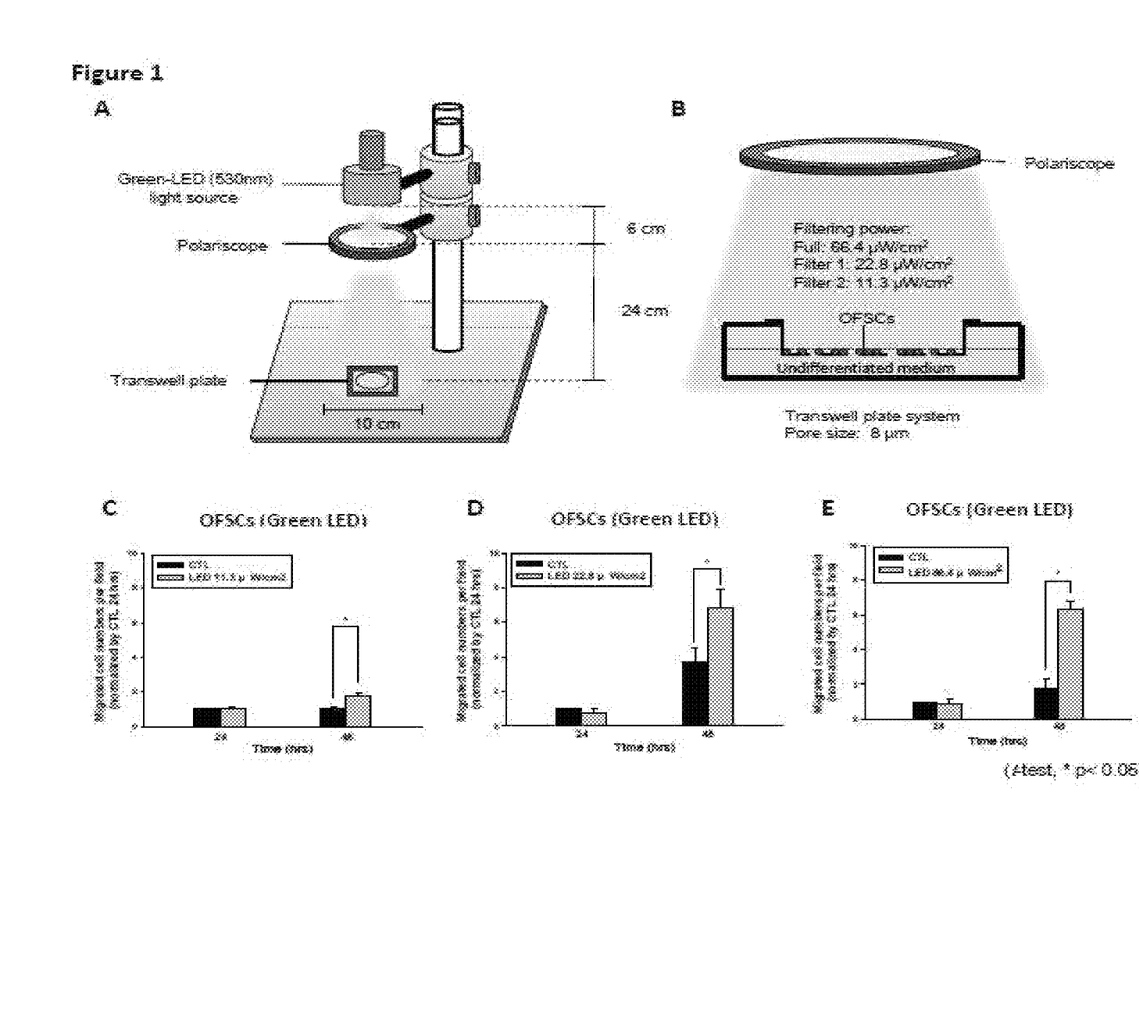
FIG. 1 shows that green light-emitting diode (LED) irradiation enhances human orbital fat stem cell (OFSC) migration. (A) Schema of LED photosystem. (B) Schema of cells in transwell migration system under LED irradiation. Green LED enhanced OFSC migration ability after 48-hour irradiation with power density of 66.4 (C), 22.8 (D) and 11.3 (E) µW/cm$^2$.

The LED photosystem is illustrated in FIG. 1. OFSCs (7500 cells/transwell) or HCE-T cells (5000 cells/transwell) were seeded on the upper surface of 8 μm pore sized transwell culture plate (PI8P01250, Millipore Millicell® cell culture insert, Millipore, Billerica, Mass., USA). The attached cells were covered by undifferentiated medium (MesenPro, Ivitrogen) (FIG. 1B) and exposed to a 530-nm green LED (M530L2, Thorlabs, Inc., Newton, N.J., USA) or a 625-nm red LED (M625L2, Thorlabs) light at a distance of 30 cm away from LED light source (FIG. 1A). The full power density of LED irradiated on cells was 66.4 $\mu W/cm^2$ and the power density could be reduced to 22.8 (filter 1) or 11.3 (filter 2) $\mu W/cm^2$ by a polariscope at 6 cm from the light. Cells in the transwell system under dark at the same time points served as the time-matched control.

Cell Migration Assay

The cells in the transwell system were under LED irradiation or dark control with or without 25 μM of ERK inhibitor (328005, Merck, Whitehouse Station, N.J., USA) for 24 or 48 hours. In this transwell migration system, migrated cells were defined by cells migrating to the bottom surface of transwell plate, while non-migrated cells were defined by cells remaining on the upper surface of transwell plate.

For migrated cell (or non-migrated cell) counting and staining, cells on the upper surface (or on the bottom surface) of transwell culture plate were totally removed by a scraper. Cells migrated to the bottom surface (or remained on the upper surface) were fixed by 3.7% formaldehyde for 20 min, and then stained by TRITC-labeled phalloidin (1:500; Sigma-Aldrich, St. Louis, Mo., USA) at 37° C. for 1 hour, followed by 4-,6-diamidino-2-phenylindole (DAPI) for 5 minutes. Migrated cells on the bottom surface were counted under a fluorescence microscopy (Leitz, Germany) with 100× magnification. The migrated cell number in each sample was determined, and the mean value was determined from cell numbers in ten random fields. More than three independent experiments were performed for each condition.

Cell Proliferation Assay

Cells were seeded in a 96-well plate (2000 cells/well) for 4 hours before being exposed to LED light or ERK inhibitor. After green LED irradiation for 24, 48, 72 hours or incubation with ERK inhibitor (328005, Merck) for 48 hours, the culture medium in each well was then replaced by 100 μl of serum-free DMEM and 20 μl MTS reagent (Promega, Madison, Wis., USA). The signal at OD490 was measured by using a microplate reader (Bio-Rad, Hercules, Calif., USA) after cells were incubated in the dark at 37° C. for another 1 to 4 hours.

Gene Expressions

RNAs were extracted using the RNeasy Kit (Qiagan Inc., Valencia, Calif., USA) followed by reversely transcribed to cDNA using an Advantage RT-for-PCR kit (Clontech, Palo Alto, Calif., USA). cDNA was amplified using a Mastercycler Gradient 5331 Thermal Cycler (Eppendorf, Germany). For microarray analysis, the differential gene expressions were detected by GeneChip™ (Affymetrix, Santa Clara, Calif., USA) and analyzed by Affymetrix Microarray Suite 5.0. For real-time RT-PCR, gene expression level was represented by monitoring the fluorescence signals after each cycle with an ABI 7300 Real-Time PCR system (Applied Biosystems). Primers used for real-time RT-PCR were listed in Table 1.

Intracellular ATP Content

Intracellular ATP level was measured using ATP determination kit (Invitrogen) as per the manufacturer's instructions. Briefly, cells were trypsinized, resuspended in CelLytic™ MT mammalian tissue lysis/extraction reagent (100 ul; Sigma-Aldrich) to release the intracellular ATP. The supernatant (10 μl) was then transferred into a 96-well cell culture cluster (Corning Costar, N.Y., USA) containing 90 μl ATP standard reaction solution and measured by Luminoskan Ascent Luminometer (Thermo Electron Corp., Waltham, Mass., USA).

Intracellular Kinase Activity

Intracellular kinase activity was determined by using human phospho-kinase array kits (R&D system, Minneapolis, Minn., USA) and Western blot analysis according to the manufacturer's instructions. Briefly, cells were trypsinized and resuspended in lysis buffer to obtain the cell lysate. For kinase array, each cell lysate (300 μg) was incubated individually with the antibody-pre-coated membrane overnight. After washing, the membrane was incubated with biotinylated-labeled antibody cocktail for 2 hours, and then incubated with streptavidin-HRP for another 30 minutes.

For Western blot analysis, 30 μg of protein was separated on 10% SDS-PAGE and blotted onto PVDF membrane (Amersham Biosciences, Uppsala, Sweden), followed by blocking with 5% skim milk in TBST buffer (50 mM Tris-HCl, 150 mM NaCl, 0.1% Tween 20, pH 7.4). The membrane was then blotted with indicated primary antibodies such as ERK (1:1000, Cell signaling, Danvers, Mass., USA), p-ERK (1:2000, Cell signaling) and α-tubulin (1:10000, Sigma-Aldrich). After 3 times of washes, the membrane was incubated with the HRP-conjugated secondary antibody (1:5000, Santa Cruz, Santa Cruz, Calif., USSA). The signals on each membrane was detected by ECL chemiluminescent reagent (PerkinElmer Life Sciences, Inc.) and their intensities were quantitatively measured by a densitometry (LabWorks, UVP Inc., Upland, Calif., USA).

Temperature Measurement

Temperature of medium was measured under dark or LED light exposure using high-sensitivity glass probe thermistor (SP31A, Sensor Scientific, Inc., Fairfield, N.J., USA). Temperature was recorded every two hours, and calibration of thermistors was performed before temperature measurement at each time point according to the manufacturer's instructions.

Statistical Analysis

Statistical analyses were performed using the Statistical Package for Social Science software (v. 16, SPSS Inc., Chicago, Ill.). Differences in viability with and without ERK inhibitor, kinase activities, temperature or migrated cell numbers between LED irradiation and dark control at the same time point were assessed using the two-tailed, non-paired t-test, and for significance, P-values <0.05. Differences among the migrated cells numbers and intracellular ATP content at various temperatures, viability or migrated cell numbers with and without LED irradiation at various time points, or data from the gene expression levels (i.e. RhoA, retinal pigment epithelium-derived rhodopsin homolog (RRH), short-wave-sensitive opsin 1 (OPN1SW), and encephalopson (OPN3)), and ATP content in migrated and non-migrated cells with and without LED irradiation were assessed using analysis of variance, Tukey's post-hoc test, and a 95% confidence level. Different characters represented different levels of significance, and level "ab" indicated statistical level in between level "a" and level "b". Error bars shown in all figures represent standard deviation of mean values.

Example 1

Effect of Green LED Irradiation on OFSC Migration

Figure 2:
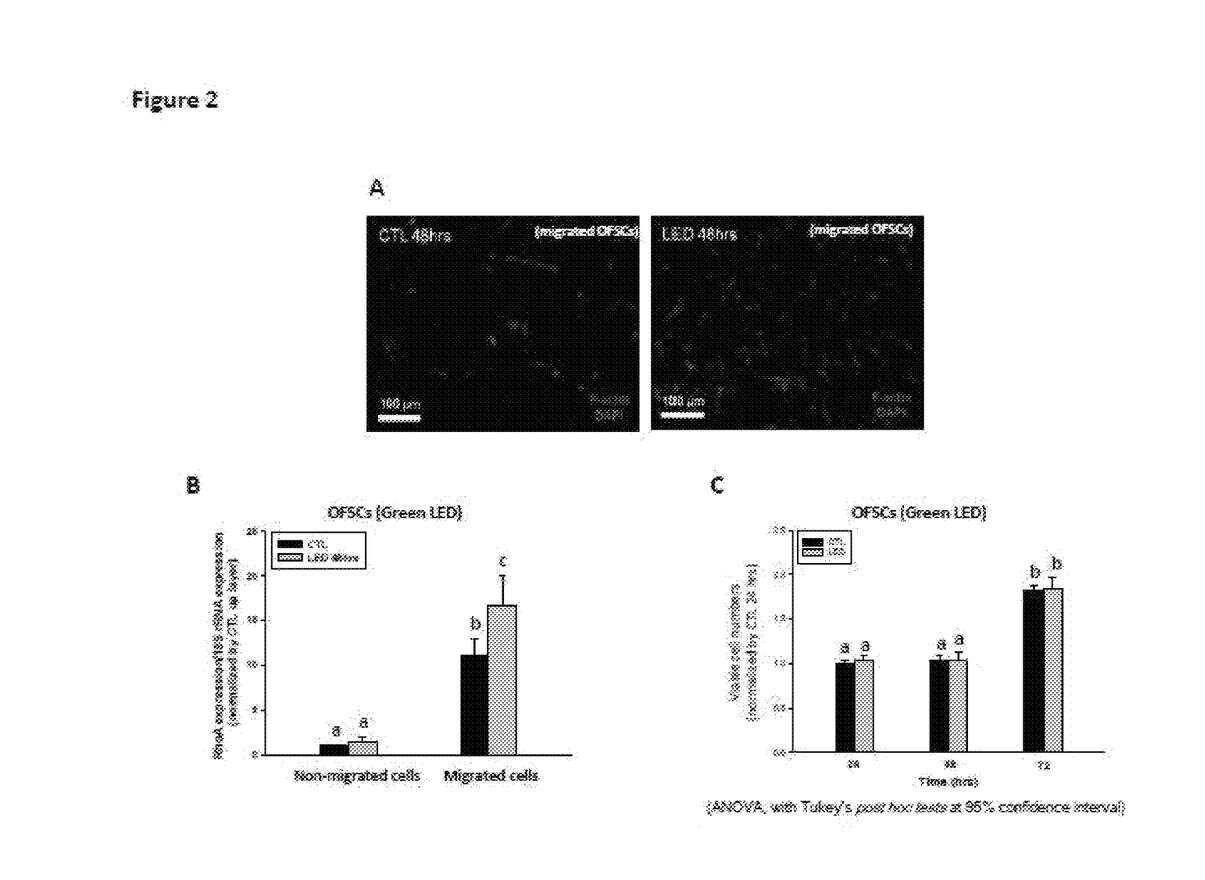
FIG. 2 shows that green LED irradiation-induced OFSC migration is associated with F-actin reorganization, and not a consequence of cell division. (A) F-actin signal in migrated OFSCs under green LED irradiation (right) was stronger than which in migrated OFSCs under dark control (left). (B) RhoA expression was up-regulated in migrated OFSCs, and green LED irradiation further increased RhoA expression in migrated OFSCs. (C) The doubling time of OFSCs was in between of 48 to 72 hours, and green LED irradiation did not affect OFSC viability.

The study design is illustrated in FIGS. 1A and B. The orbital fat stem cells were initially seeded on the upper surface of the transwell plate. The cells that have migrated to the bottom surface of the transwell plate are designated as migrated cells, while non-migrated cells are cells remaining on the upper surface. Compared to time-matched dark control, 48 hours of Actin cytoskeleton re-organization is essential for cell migration (Papakonstanti E A, Stournaras C. FEBS Lett. 2008; 582:2120-7) and the formation of actin stress fibers during cell migration is regulated by RhoA (Fukata M et al., Curr Opin Cell Biol. 2003; 15:590-7; Evers E E et al, Eur J Cancer. 2000; 36:1269-74). After 48 hours of green LED irradiation, F-actin signals in migrated OFSCs (FIG. 2A, right) were stronger than in migrated cells under dark (FIG. 2A, left). Green LED irradiation significantly up-regulated RhoA expression in migrated OFSCs, but did not alter the RhoA expression in non-migrated cells (FIG. 2B).

Effect of Green LED Irradiation on OFSC Proliferation

To determine whether green LED irradiation affected cell proliferation, the numbers of viable OFSCs under green LED light exposure at various time points were measured by MTS assay. As shown in FIG. 2C, OFSC number doubled between 48 and 72 hours both in the dark and under green LED exposure; thus, LED irradiation showed no effect on OFSC proliferation.

To avoid the contribution of cell division to increase in migrated cell numbers, we performed the following experiments under LED exposure for up to 48 hours at the power density of 66.4 $\mu W/cm^2$.

Effect of Green LED Irradiation on HCE-T Cell Migration

Figure 3:
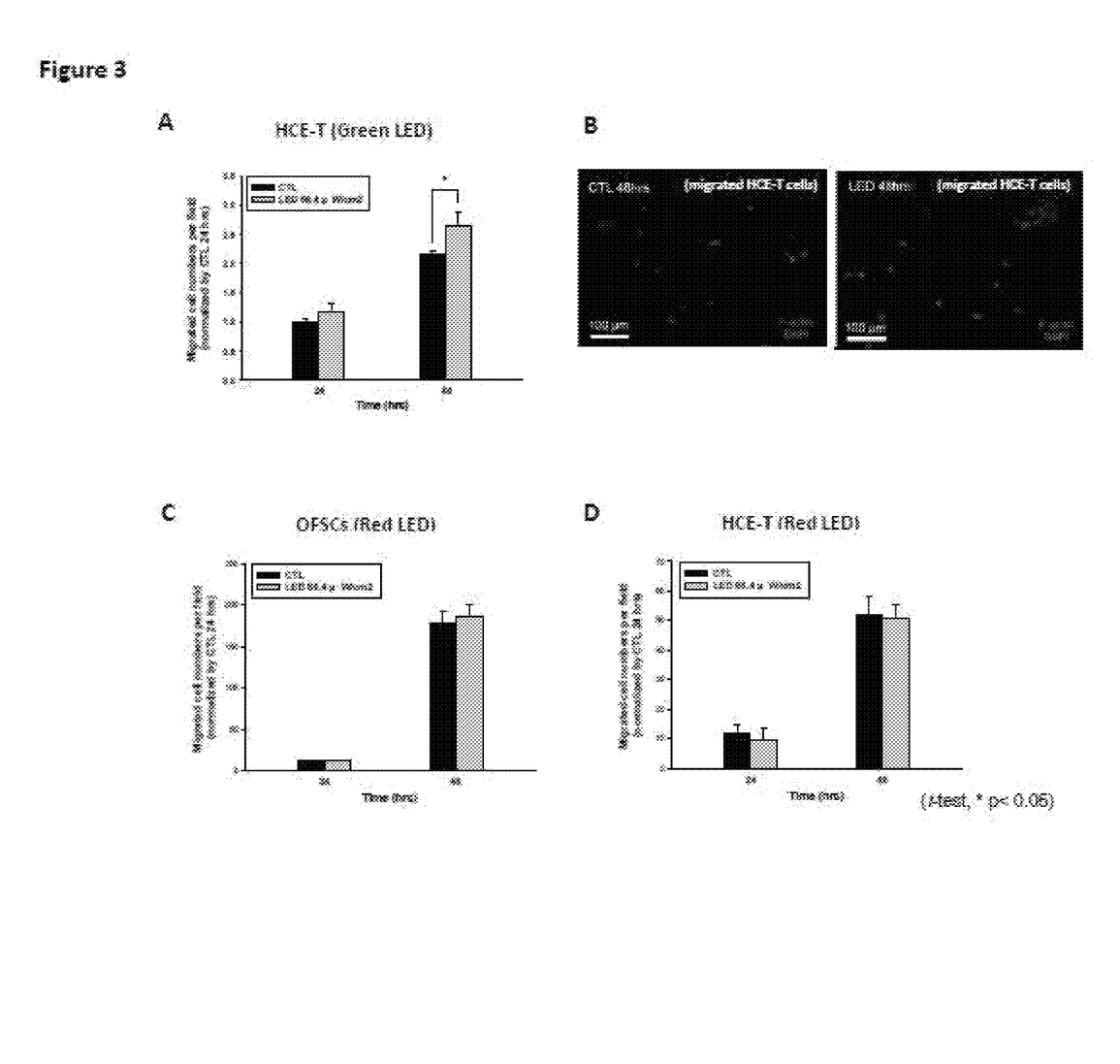
FIG. 3 shows that LED irradiation-induced cell migration is wavelength specific. Green LED irradiation enhanced human corneal epithelial (HCE-T) cells migration (A), and F-actin signal in migrated HCE-T cells was not significantly increased by green LED irradiation (B). Red LED irradiation neither altered the migration ability in OFSCs (C) nor in HCE-T cells (D).

To test the cell specificity of the induction of migration by green LED irradiation, OFSCs were replaced by HCE-T cells, which are well-differentiated cornel epithelial cells, in the LED photosystem. HCE-T cell migration was also enhanced under 66.4 $\mu W/cm^2$ of green LED irradiation for 48 hours, but the increase over this time period was less than 1.5 fold (FIG. 3A), as compared with the 3-fold increase for the OFSCs (FIG. 1C). Light-driven F-actin reorganization in migrated OFSCs (FIG. 2A) was also more prominent than in migrated HCE-T cells (FIG. 3B).

Role of Wavelength on LED Irradiation-Induced Cell Migration

To further dissect the role of wavelength in such a photoinduced cell migration, green LED (530 nm) was replaced by red LED (625 nm), which has no overlap of spectrum wavelength with the green LED light. Surprisingly, under the same power density to green LED irradiation (66.4 $\mu W/cm^2$), red LED irradiation for 48 hours neither affected OFSC (FIG. 3C) nor HCE-T cell (FIG. 3D) migration in the photosystem.

ATP Content in Green LED Irradiated OFSCs

Figure 4:
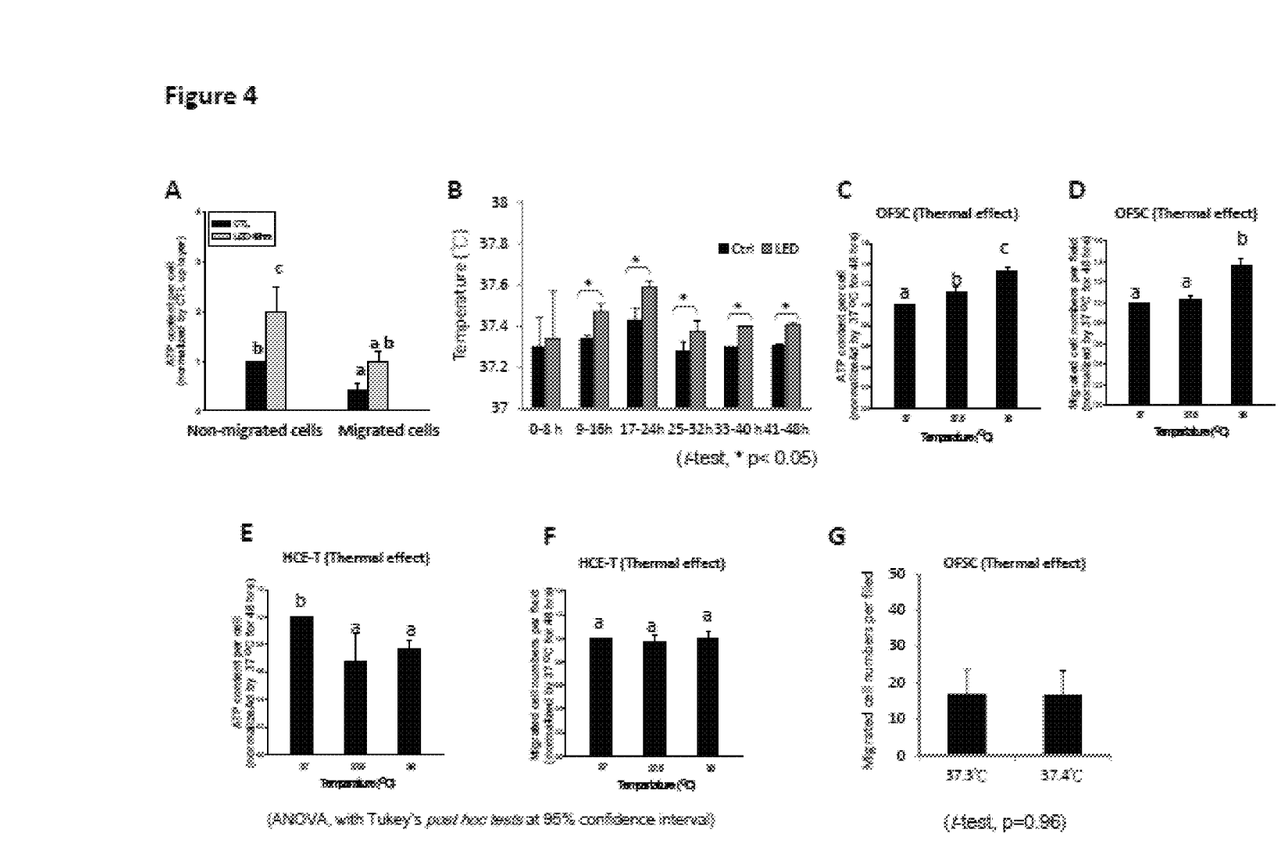
FIG. 4 shows that thermal effect partially contributes in green LED irradiation-induced ATP production for OFSC migration. (A) Green LED irradiation increased intracellular ATP production by 2 folds in both migrated and non-migrated OFSCs, and ATP consumption was observed during cell migration. (B) Green LED irradiation increased the temperature by 0.1° C. after 8-hour of light exposure. (C) Elevation of temperature by heat up to 0.5° C. and above significantly increased ATP content in OFSCs. (D) Elevation of temperature by heat up to 1° C. significantly increased OFSC migration. Heat-induced thermal effect neither changed the ATP content in HCE-T cells (E) nor HCE-T motility (F). Elevation of temperature from 37.3° C. to 37.4° C. by heat did not alter the migration potential in OFSCs (G).

Migration is an energy consumption behavior for a cell. ATP is essential for phosphorylation of most protein kinases [34] and increases the formation of guanosine triphosphate (GTP) by transferring phosphate to GDP under light stimulation (Tanaka N et al., J Photochem Photobiol B. 1998; 45:113-21). Besides, ATP may form cyclic adenosine monophosphate (cAMP) by conformational change (Schwartz P A et al., Bioorg Chem. 2011; 39:192-210). We further investigated the effect of green LED irradiation on ATP production and OFSCs migration. As shown in FIG. 4A, green LED irradiation markedly increased ATP production in both migrated and non-migrated OFSCs. Compared to non-migrated cells, however, the intracellular ATP content in migrated OFSCs was significantly lower, suggesting that ATP was utilized during cell migration.

Alteration of Temperature in Green LED Irradiated OFSCs

Thermal stress has been reported to increase ATP production from mitochondria (Rivera R M et al., Reproduction. 2004; 128:33-42). Monitoring the temperature in the culture medium at various time points under green LED irradiation and dark control showed that green LED irradiation significantly elevated local temperature after 8 hours of light exposure. In average, the medium temperature under green LED irradiation (37.4° C.) was only 0.1° C. higher than dark control (37.3° C.) in the first 48 hours (FIG. 4B), and which was associated with increase in 100% of ATP production in OFSCs (FIG. 4A).

Thermal Effect on ATP Production and Cell Migration

To determine the role of thermal effect on ATP production and cell migration, we increased culture medium temperature by heat instead of LED light for 48 hours. As showed in FIGS. 4C-F, responses of ATP production and cell migration to thermal effect could be observed only in OFSCs (FIGS. 4C and D), but not HCE-T cells (FIGS. 4E and F). Elevation of 1.0° C. by heat was associated with a 30% increase of ATP production in OFSCs (FIGS. 4C and D), and this temperature effect on ATP production was not seen in HCE-T cells (FIGS. 4E and F). However, elevation of 0.1° C. (from 37.3° C. to 37.4° C.) by heat did not alter the migration potential of OFSCs (FIG. 4G), indicating that the green LED irradiation-induced ATP production and cell migration were not attributable to thermal stress.

Phototransduction for Green LED Irradiation-Induced OFSC Migration

Figure 5:
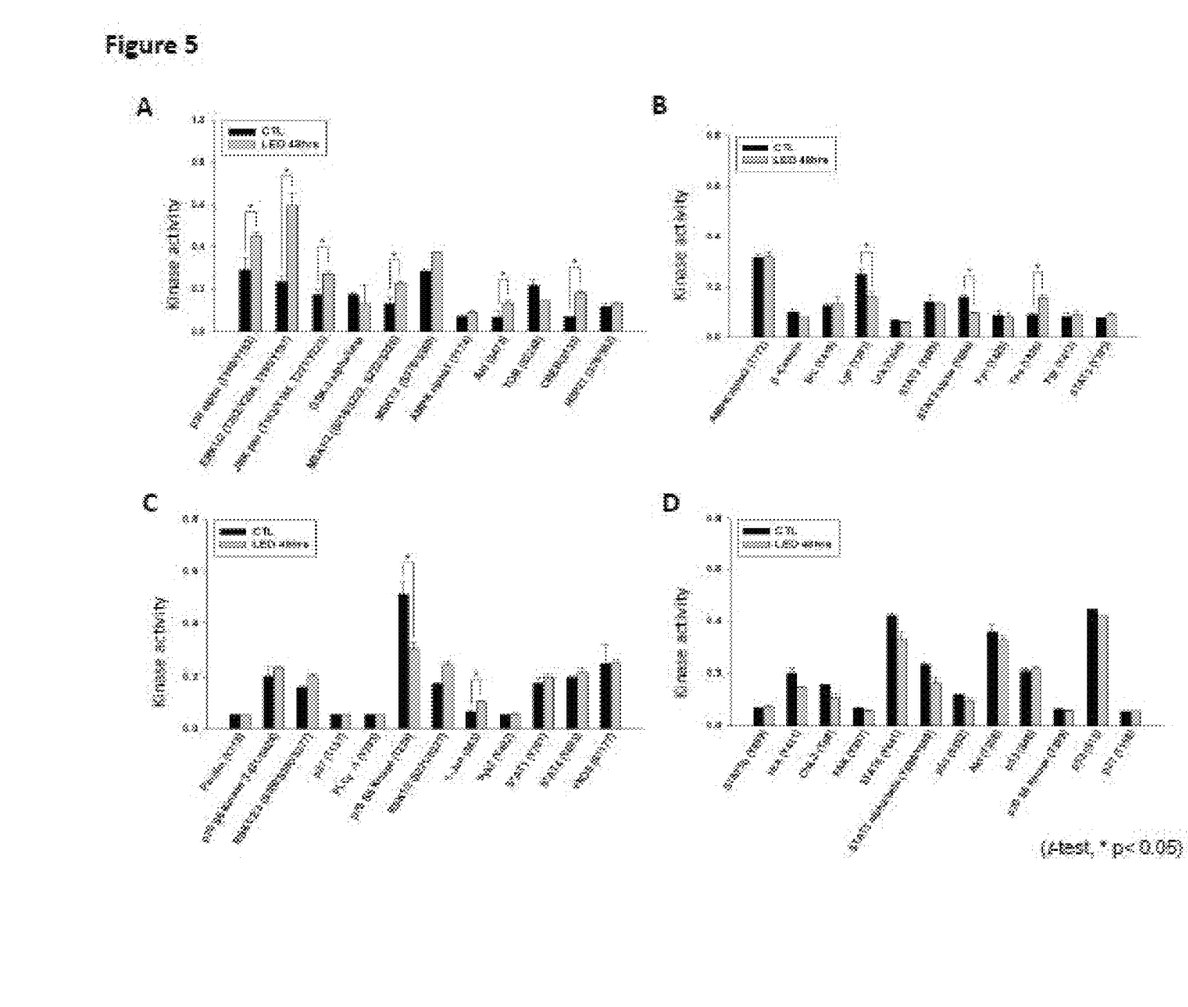
FIG. 5 shows that green LED irradiation significantly activates ERK/MAPK/p38 signaling pathway in OFSCs. After 48 hours of green LED irradiation, intracellular kinase activities of p38, ERK1/2, JNK, MEK1/2, Akt, CREB (A), Yes (B), and c-Jun (C) were significantly increased, while Lyn, STAT 5 alpha (B), and p70S6 kinase (C) were decreased. (D) Kinases involved in cell cycle such as p53, p27 and TOR were not affected.

Since green LED irradiation increased ATP production, and ATP was utilized for OFSC migration (FIG. 4A), we looked for the target(s) of increased ATP during cell migration promoted by green LED irradiation. Human phosphorylated kinase array was performed to analyze the differential kinase activities in OFSCs between green LED irradiation and dark control. We found that eight of the kinases, i.e., p38, ERK 1/2, c-Jun N-terminal kinase (JNK), MAP kinase kinase (MEK) 1/2, Akt, cAMP response element-binding (CREB) (FIG. 5A), Yes (FIG. 5B), and c-Jun (FIG. 5C) were markedly activated after 48-hour green LED irradiation, while three of the kinases, i.e., Lyn, signal transducer and activator of transcription (STAT) 5 alpha (FIG. 5B), and p70S6 kinase (FIG. 5C) were inhibited. Kinases involved in cell cycle, such as p53, p27 and TOR, were not affected by green LED irradiation (FIG. 5D).

Figure 6:
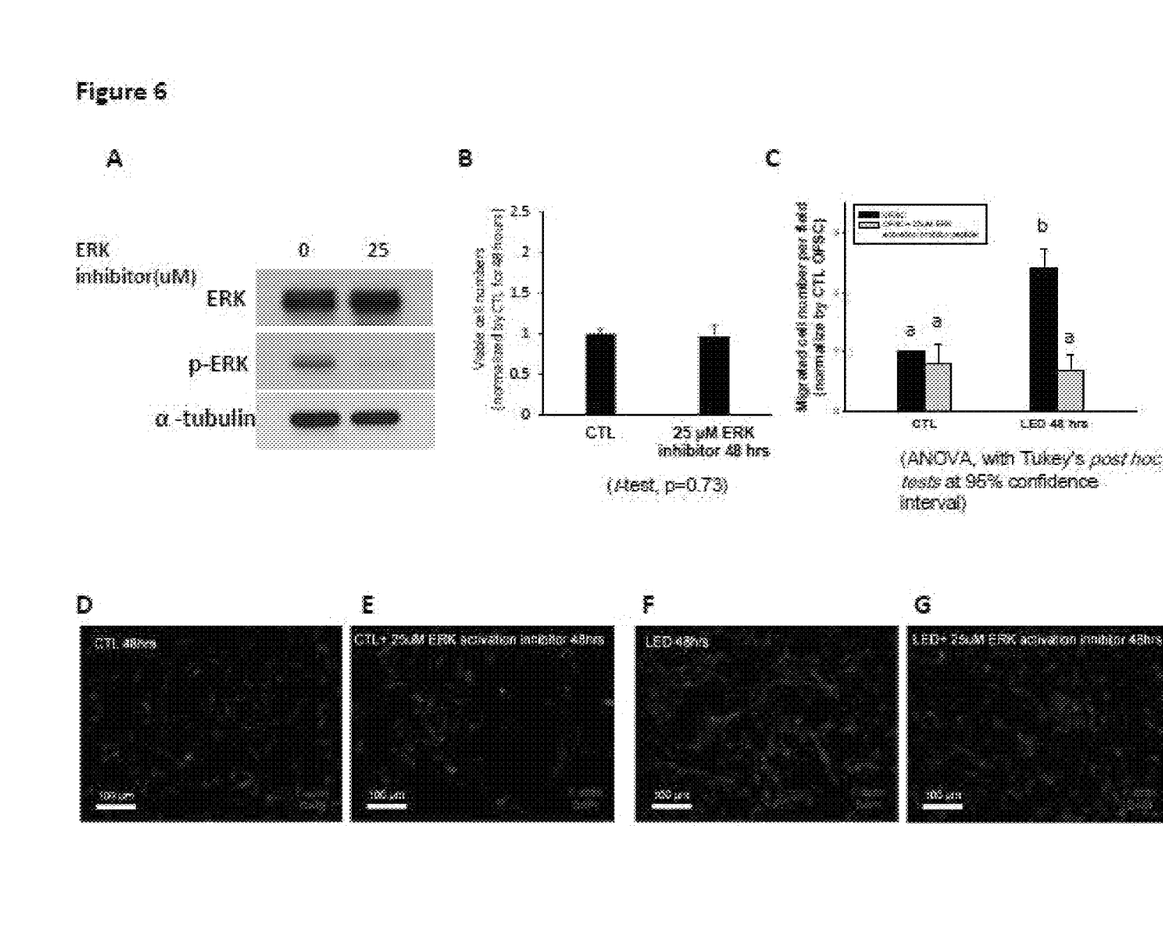
FIG. 6 shows that inhibition of ERK activity abrogates green LED irradiation-induced OFSC migration. (A) Twenty-five μM ERK inhibitor blocked ERK phosphorylation in OFSCs within 2 hours. Persistent treatment of 25 μM ERK inhibitor did not affect OFSC viability (B), but totally abrogated green LED irradiation-induced OFSC migration in the first 48 hours (C). (D, E) Under dark control, inhibition of ERK activity did not change F-actin organization in migrated OFSCs. (F, G) Under green LED irradiation, inhibition of ERK activity significantly affected F-actin re-organization in migrated OFSCs.

To assess the role of ERK signaling pathway in the green LED irradiation-induced OFSC migration, intracellular ERK activity was inhibited by using an ERK activation inhibitor peptide II that targets the phosphorylation of ERK (FIG. 6A). OFSC viability was not affected by the ERK inhibitor (25 $\mu M$) over the 48 hours of study (FIG. 6B). The inhibition of ERK activity selectively abrogated the green LED irradiation-induced OFSC migration, but had no effect on cell migration in the dark control (FIG. 6C). The ERK inhibitor also decreased F-actin signals in the migrated cells triggered by green LED irradiation (FIGS. 6F and G) and did not affect F-actin in the migrated cells under dark (FIGS. 6D and E).

Photosensitizers for Green LED Irradiation-Induced OFSC Migration

Figure 7:
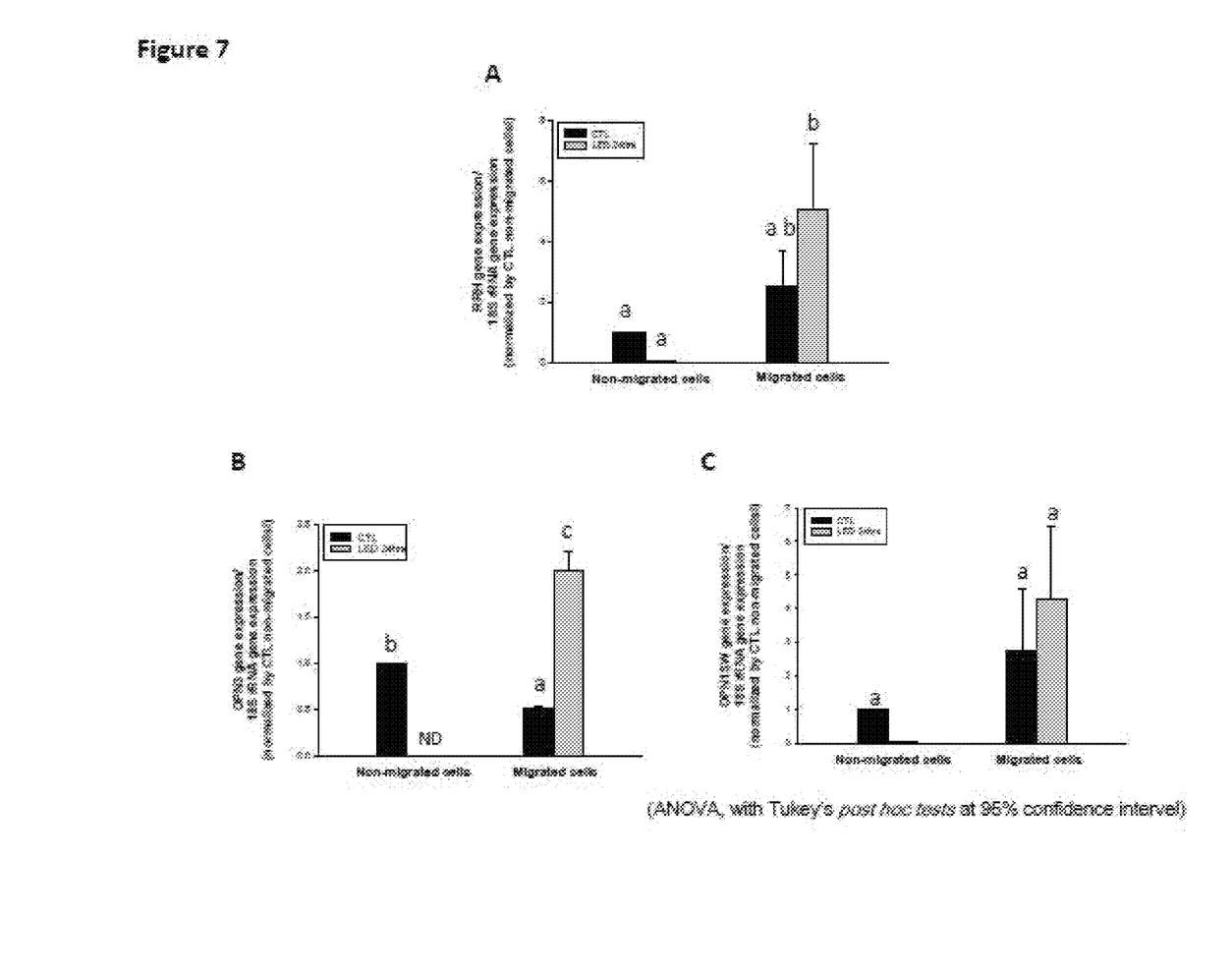
FIG. 7 shows that upregulation of RRH and OPN3 in OFSCs accompanies green LED irradiation induced cell motility. OFSCs expressed three photosensitizers, which were RRH (A), OPN3 (B) and OPN1SW (C). After green LED irradiation, gene expressions of RRH (A) and OPN3 (B) were upregulated in migrated OFSCs, but not in non-migrated OFSCs. (C)OPN1SW was not sensitive to green LED irradiation.

To find out the putative photosensitive molecules that directed the green LED irradiation-induced OFSC migration, microarray analysis was used for screening the basal expression level of opsins (OPNs), the photosensitizers in animal cells (Terakita A. *Genome Biol.* 2005; 6:213), in OFSCs. As shown in Table 2 listing the human opsins have been identified, gene expressions of RRH, OPN1SW, OPN3 and OPN5 were detectable by at least one probe on the microarray chip. OFSCs did not express rhodopsin (OPN2), long/medium-wave-sensitive opsin 1 (OPN1LW/OPN1MW), ChR2, melanopsin (OPN4), neuropsin (KLK8), or retinal G protein coupled receptor (RGR). Real-time RT-PCR was performed on the photosensitizers detected by microarray under dark and green LED irradiation for 48 hours; the results confirmed the constitutional expression of RRH, OPN1SW and OPN3, but not OPN5 (data not shown). Using transwell migration assay, we found upregulation of RRH (FIG. 7A) and OPN3 (FIG. 7B), but not OPN1SW (FIG. 7C), during the first 24 hours in migrated OFSCs triggered by green LED irradiation. In the dark control, the expressions of RRH (FIG. 7A) and OPN1SW (FIG. 7C) were not significantly different between non-migrated and migrated OFSCs. OPN3 expression was decreased in migrated OFSCs under dark control in comparison of non-migrated OFSCs (FIG. 7B).

What is claimed is:

1. A method of enhancing a directional migration of stem cells, comprising providing one or more stem cell(s) and irradiating the stem cells with an effective energy of green light thereby enhancing stem cell directionally migrating, wherein the orientation of migration of stem cells is opposite to the green light source.

2. The method of claim 1, wherein the irradiation of green light is provided at an energy level of about 0.5 J/cm$^2$ to about 30 J/cm$^2$.

3. The method of claim 1, wherein the irradiation of green light is provided at an energy level of about 1.95 J/cm$^2$ to about 11.4 J/cm$^2$.

4. The method of claim 1, wherein the energy level is green light emitting diode (LED), green fluorescence or laser.

5. The method of claim 1, wherein the stem cells are embryonic stem cells or adult stem cells.

6. The method of claim 5, wherein the adult stem cell is hematopoietic stem cells (HSCs), mesenchymal stem cells (MSCs), adipose-derived stem cell, endothelial stem cell and dental pulp stem cells.

7. The method of Claim 6, wherein the adipose-derived stem cell is orbital fat stem cell (OFSC).

8. A stem cell produced by the method of claim 1, which has higher ATP contents then the stem cell untreated by the method of claims 1 and p38, ERK ½, c-Jun N-terminal kinase (JNK), MAP kinase kinase (MEK) ½, Akt, cAMP response element-binding (CREB), Yes and c-Jun are activated.

9. The cell of claim 8, wherein Lyn, signal transducer and activator of transcription (STAT) 5 alpha, and p70S6 kinase are inhibited.

10. The cell of claim 8, wherein the expression of RRH, OPN1SW and OPN3are induced by green light.

* * * * *